US012727823B2

(12) United States Patent
Magar

(10) Patent No.: US 12,727,823 B2
(45) Date of Patent: Sep. 8, 2026

(54) CUSTOMIZABLE PATCHES

(71) Applicant: LIFESIGNALS, INC., Fremont, CA (US)

(72) Inventor: Surendar Magar, Dublin, CA (US)

(73) Assignee: LIFESIGNALS, INC., Milpitas, CA (US)

(*) Notice: Subject to any disclaimer, the term of this patent is extended or adjusted under 35 U.S.C. 154(b) by 294 days.

(21) Appl. No.: 18/647,155

(22) Filed: Apr. 26, 2024

(65) Prior Publication Data

US 2024/0341685 A1 Oct. 17, 2024

Related U.S. Application Data

(63) Continuation of application No. 16/849,774, filed on Apr. 15, 2020, now abandoned, which is a (Continued)

(51) Int. Cl.
*A61B 5/00* (2006.01)
*A61B 5/0205* (2006.01)
(Continued)

(52) U.S. Cl.
CPC .......... *A61B 5/6833* (2013.01); *A61B 5/0022* (2013.01); *A61B 5/0024* (2013.01);
(Continued)

(58) Field of Classification Search
CPC . A61B 5/6833; A61B 5/0022; A61B 5/02055; A61B 5/112; A61B 5/14542;
(Continued)

(56) References Cited

U.S. PATENT DOCUMENTS 8,764,651 B2 7/2014 Tran
11,076,792 B2 8/2021 Tompkins et al.
(Continued)

FOREIGN PATENT DOCUMENTS

CN 101742981 A 6/2010
CN 103781404 A 5/2014
(Continued)

OTHER PUBLICATIONS

EP18874368.6 Extended European Search Report dated Jul. 1, 2021.

(Continued)

*Primary Examiner* — Eugene T Wu
(74) *Attorney, Agent, or Firm* — WILSON SONSINI GOODRICH & ROSATI

(57) ABSTRACT

A compact integrated patch may be used to collect physiological data. The patch may be wireless. The patch may comprise a plurality of sensors, each sensor configured to collect different health related data from a subject to which the patch is attached, and a communication interface configured to wirelessly and directly communicate with a mobile device, wherein the mobile device is capable of running a plurality of applications, wherein each application of said plurality is configured to utilize data from different subsets of sensors from the plurality of sensors, to provide different monitoring activities for the subject. The patch may be utilized in everyday life as well as in clinical environments.

20 Claims, 7 Drawing Sheets

Related U.S. Application Data continuation of application No. PCT/US2018/058290, filed on Oct. 30, 2018.

(60) Provisional application No. 62/579,309, filed on Oct. 31, 2017.

(51) Int. Cl.

| | |
|---|---|
| ***A61B 5/11*** | (2006.01) |
| ***A61B 5/145*** | (2006.01) |
| ***A61B 5/16*** | (2006.01) |
| ***A61B 7/04*** | (2006.01) |
| *A61B 5/024* | (2006.01) |
| *A61B 5/0245* | (2006.01) |
| *A61B 5/08* | (2006.01) |

(52) U.S. Cl.

CPC .......... *A61B 5/02055* (2013.01); *A61B 5/112* (2013.01); *A61B 5/14542* (2013.01); *A61B 5/165* (2013.01); *A61B 5/4818* (2013.01); *A61B 5/4875* (2013.01); *A61B 5/681* (2013.01); *A61B 5/7264* (2013.01); *A61B 5/742* (2013.01); *A61B 7/04* (2013.01); *A61B 5/02405* (2013.01); *A61B 5/0245* (2013.01); *A61B 5/0816* (2013.01); *A61B 2503/04* (2013.01); *A61B 2503/08* (2013.01); *A61B 2503/40* (2013.01); *A61B 2560/0443* (2013.01); *A61B 2562/0219* (2013.01)

(58) Field of Classification Search

CPC ..... A61B 5/165; A61B 5/4818; A61B 5/4875; A61B 5/681; A61B 5/7264; A61B 5/742; A61B 7/04; A61B 5/02405; A61B 5/0245; A61B 5/0816; A61B 2503/04; A61B 2503/08; A61B 2503/40; A61B 2560/0443; A61B 2562/0219; A61B 2560/0412; A61B 2560/045; A61B 5/0205; A61B 5/00; G16H 40/67

See application file for complete search history.

(56) References Cited

U.S. PATENT DOCUMENTS

| | | | |
|---|---|---|---|
| 2008/0167535 | A1 | 7/2008 | Stivoric et al. |
| 2009/0051544 | A1 | 2/2009 | Niknejad |
| 2009/0062670 | A1 | 3/2009 | Sterling et al. |
| 2011/0028814 | A1 | 2/2011 | Petersen et al. |
| 2011/0172545 | A1 | 7/2011 | Grudic et al. |
| 2012/0030547 | A1 | 2/2012 | Raptis et al. |
| 2013/0060098 | A1 | 3/2013 | Thomsen et al. |
| 2013/0116520 | A1 | 5/2013 | Roham et al. |
| 2014/0080207 | A1 | 3/2014 | Lipkens et al. |
| 2014/0213876 | A1 | 7/2014 | Banet et al. |
| 2015/0335288 | A1 | 11/2015 | Toth et al. |
| 2016/0029906 | A1 | 2/2016 | Tompkins et al. |
| 2016/0095060 | A1 | 3/2016 | Seddighrad et al. |
| 2016/0324442 | A1 | 11/2016 | Zdeblick |
| 2017/0021172 | A1 | 1/2017 | Perez et al. |
| 2017/0080207 | A1 | 3/2017 | Perez et al. |
| 2017/0164876 | A1* | 6/2017 | Hyde .................. A61B 5/1118 |
| 2017/0258402 | A1 | 9/2017 | Acquista et al. |

FOREIGN PATENT DOCUMENTS

| | | | |
|---|---|---|---|
| KR | 20170075012 | A | 6/2017 |
| WO | WO-2008098346 | A1 | 8/2008 |
| WO | WO-2012176193 | A1 | 12/2012 |
| WO | WO-2016010983 | A1 | 1/2016 |
| WO | WO-2016070128 | A1 | 5/2016 |
| WO | WO-2017039518 | A1 | 3/2017 |
| WO | WO-2017155369 | A1 | 9/2017 |
| WO | WO-2017173462 | A1 | 10/2017 |
| WO | WO-2019089652 | A1 | 5/2019 |

OTHER PUBLICATIONS

PCT/US2018/058290 International Search Report and Written Opinion dated Jan. 4, 2019.

U.S. Appl. No. 16/849,774 Office Action dated Oct. 31, 2023.

U.S. Appl. No. 16/849,774 Office Action dated Aug. 20, 2021.

U.S. Appl. No. 16/849,774 Office Action dated Feb. 16, 2023.

U.S. Appl. No. 16/849,774 Office Action dated Jul. 19, 2022.

* cited by examiner

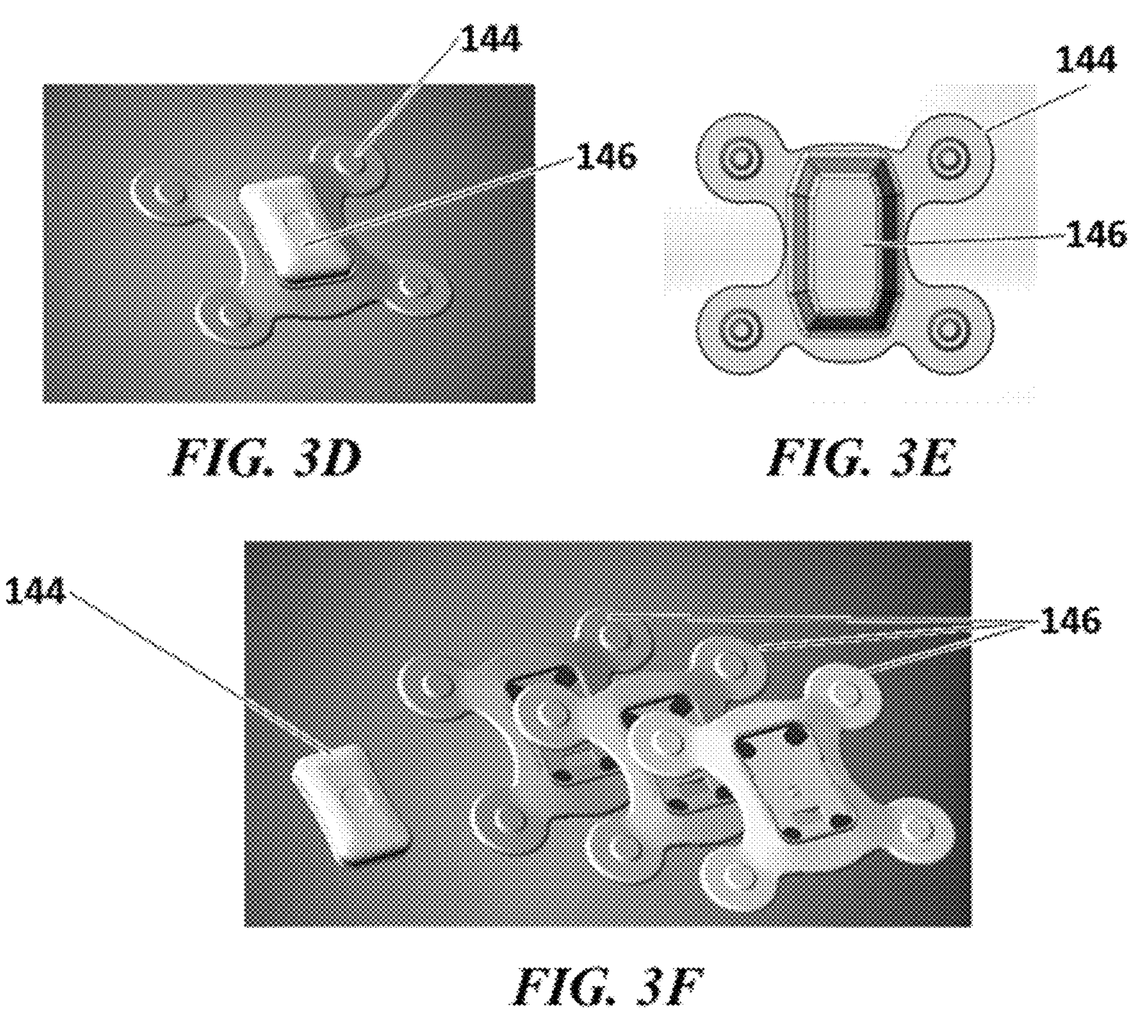
FIG. 3D
FIG. 3E
FIG. 3F
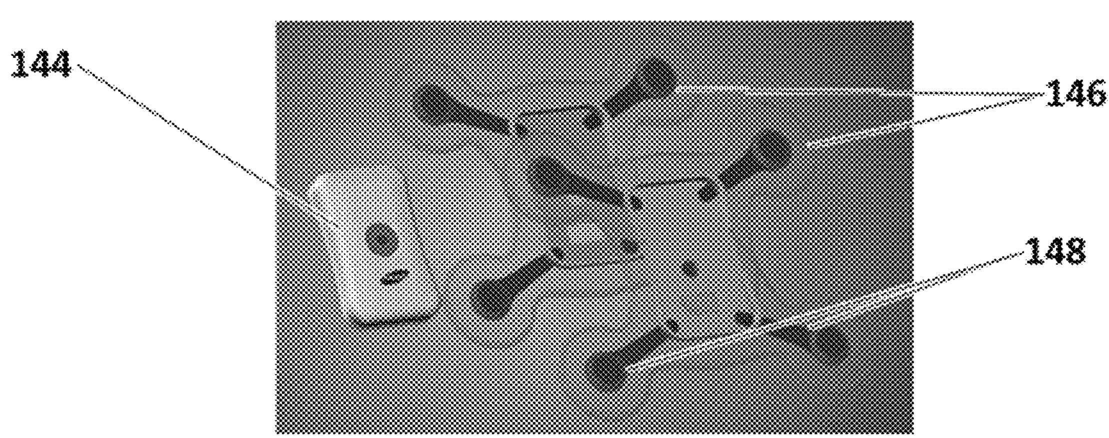
FIG. 3G

CUSTOMIZABLE PATCHES

CROSS-REFERENCE

This application is a continuation of U.S. application Ser. No. 16/849,774, filed on Apr. 15, 2020, which is a continuation of International Patent Application No. PCT/US18/58290, filed on Oct. 30, 2018, which claims the benefit of U.S. Provisional Patent Application No. 62/579,309, filed Oct. 31, 2017, each of which is incorporated herein by reference in its entirety.

BACKGROUND

Monitoring physiological conditions of the human body is an important component of health care. Increasingly, with sophistication of technology related to sensors and wireless communication, electronics that monitor physiological conditions may become integrated with everyday life and be utilized for purposes of maintaining a healthy lifestyle and/or managing illness.

In some instances, remote health monitoring makes it easier and cost effective to monitor the health of vast populations. Wireless systems may be desirable to enable remote health monitoring. Conventional wireless health monitoring systems may be bulky, expensive, have inadequate wireless link reliability, or may have high power dissipation which limits their applications, e.g., to monitoring a wide range of physiological parameters in high volumes for large populations. In some instances, health monitoring systems may inadequately account for concurrent use with other forms of medical equipment such as defibrillators.

SUMMARY

Often, wireless health monitoring systems may be directed to achieving a fixed application or objective (e.g., monitoring heart rate, monitoring temperature, etc.), and the associated hardware (e.g., sensors, etc.) and software (e.g., measurement parameters and signal processing, etc.) may be engineered specifically to achieve only the fixed application. For example, such systems may be restricted to only a single application or objective. These systems may not be compatible with other, different applications or objectives, and lack significant flexibility in use. In most cases, the entire system (e.g., device, program, etc.) may have to be deconstructed and/or reconstructed to accommodate the different applications, including making hardware modifications and software modifications. Such retroactive procedures can be very costly, inefficiently, and time-consuming.

Technologies disclosed herein may overcome drawbacks, such as those described above, in the existing physiological monitoring systems. The technologies may miniaturize electrodes and data collection devices into a compact wireless platform that can be attached to a subject. A wireless platform can comprise a plurality of sensors and a communication interface which can wirelessly and directly communicate with an external device, such as a mobile device, capable of executing a plurality of different applications. Different sensors in the plurality of sensors may be configured to collect different types of data from the subject. Different applications in the plurality of applications can be configured to activate, transfer data to, receive data from, and/or otherwise utilize data from different combinations of the plurality of sensors integrated in the wireless platform. The wireless platform can be activated by the external device to monitor different activities via the plurality of different applications. For example, such activity monitoring can include cardiac care, sleep apnea, athlete fitness, infant monitoring, senior living, pet monitoring, gait analysis, mental stress, emotional states, and fall detection, among other activities described herein. The sensors may include clinical grade sensors. The wireless platform may be configured to allow clinically-approved placement of the sensors on the subject.

In some instances, the wireless platform may comprise at least a disposable portion (or module) and a reusable portion (or module). The disposable portion and the reusable portion may be coupled together. The disposable portion and the reusable portion can be easily decoupled. The reusable portion may be power rechargeable. The disposable portion may comprise an adhesive mechanism to allow interfacing and coupling to a skin of the subject or to a clothing of the subject.

The external device may, based on the type of application it is executing, receive data from a selected combination of sensors in the wireless platform, and analyze such data to output a result. The result may be a progress, product, or other analytics of one or more monitored activities of the application. The result may be displayed by the external device, such as via an integrated display of the external device (e.g., mobile device display) or an external display coupled to the external device. Alternatively or in addition, the result may be output in a non-visual manner, such as via auditory signals (e.g., beeping, etc.) or haptic signals (e.g., vibrations, etc.) or olfactory signals (e.g., dispensing an odor) or other non-visual signals. In some instances, the result may be delivered to and outputted by a wearable device worn by the subject. For example, such wearable device may be a watch or a band. The results may be outputted in a visual manner, such as via a display of the wearable device, and/or in a non-visible manner, such as via a speaker or actuator of the wearable device. Any process described herein may occur in real-time.

Beneficially, the wireless platform provided herein may have sufficient flexibility to accommodate and enable the monitoring of different activities, even those uncontemplated at the time of manufacture of the hardware portion of the wireless platform. Any user, such as individuals, entities, manufacturers, healthcare professionals, medical operators, and others, may design and engineer an application utilizing any combination of a plurality of sensors included in the wireless platform to achieve an objective, including clinical objectives. Such applications may be created, prior to, simultaneously, or subsequent to manufacture of the hardware portion of the wireless platform. The wireless platform may comprise a processor and/or electronic module capable of controlling the plurality of sensors in the wireless platform to comply with the requirements and instructions of the different applications executed by an external device in communication with the wireless platform via a communication interface of the wireless platform.

In an aspect, provided is a wireless medical patch comprising: a plurality of sensors, each sensor configured to collect different health related data from a subject to which the patch is attached; and a communication interface configured to wirelessly and directly communicate with a mobile device, wherein the mobile device is capable of running a plurality of applications, wherein each application of said plurality is configured to utilize data from different subsets of sensors from the plurality of sensors, to provide different monitoring activities for the subject.

In some embodiments, the plurality of sensors comprise a plurality of clinical grade sensors.

In some embodiments, the plurality of sensors comprise three of more of the following sensors: ECG, heart rate, heart rate variation, respiration, SpO2, temperature, accelerometer, gyroscope, hydration, and heart sound.

In some embodiments, the patch comprises at least one disposable portion and at least one reusable portion. In some embodiments, the disposable portion is a body layer configured to adhere to the skin of the subject. In some embodiments, the body layer comprises one or more electrical contacts configured to convey electrode data to the at least one reusable portion. In some embodiments, the reusable portion comprises one or more electronic modules. In some embodiments, the communication interface is provided on the one or more electronic modules. In some embodiments, the at least one reusable portion connects with the at least one disposable portion with aid of one or more magnets.

In some embodiments, the communication interface comprises one or more radio transmitters or receivers. In some embodiments, the communication interface comprises at least one narrowband radio transmitter, receiver, or transceiver, and at least one ultrawideband radio transmitter, receiver, or transceiver.

In some embodiments, the mobile device is a smartphone.

In some embodiments, the plurality of applications comprise at least two of the following use cases: cardiac care, sleep apnea, athlete fitness, infant monitoring, senior living, pet monitoring, gait analysis, mental stress, emotional states, or fall detection.

In some embodiments, the patch is configured to be positioned on the subject's torso to collect the health related data.

In some embodiments, the plurality of applications are capable of providing analytics for a plurality of use cases by relying on data from the plurality of sensors of the patch alone without requiring additional data from any other sensors.

In another aspect, provided is a method of monitoring health related conditions of a subject, said method comprising: receiving data from a wireless medical patch configured to be attached to the subject, wherein the patch comprises a plurality of sensors, each sensor configured to collect different health related data from the subject; analyzing the data, with aid of an application on a mobile device that utilizes the data from a first subset of sensors, wherein the mobile device is capable of running at least one other application that utilizes data from a second subset of sensors different from the first subset of sensors; and wirelessly transmitting information to be displayed on a wearable device worn by the subject.

In some embodiments, the plurality of sensors comprise a plurality of clinical grade sensors.

In some embodiments, the plurality of sensors comprise three of more of the following sensors: ECG, heart rate, heart rate variation, respiration, SpO2, temperature, accelerometer, gyroscope, hydration, and heart sound.

In some embodiments, the data is received from the wireless medical patch via radio communications.

In some embodiments, the wearable device is a watch configured to be worn on a wrist of the subject.

In some embodiments, the information is displayed on a screen of the wearable device, and wherein the information is displayed in a format based on an application type, for the application on the mobile device. In some embodiments, different application types result in different formats of information being displayed on the screen of the wearable device. In some embodiments, the format includes one or more of the following: time charts, histograms, trends over time, cool diagrams, evaluations, statements, messages, pie charts, or event markers.

In some embodiments, the method further comprises transmitting health related information to the cloud. In some embodiments, the health related information is viewable by the subject or a medical practitioner of the subject. In some embodiments, the health related information is analyzed with aid of one or more machine learning applications.

In some embodiments, selection of the application automatically results in a selection of one or more sensors from the plurality of sensors to provide the data to be analyzed.

In some embodiments, wherein the application and the at least one other application comprise at least two of the following use cases: cardiac care, sleep apnea, athlete fitness, infant monitoring, senior living, pet monitoring, gait analysis, mental stress, emotional states, or fall detection.

In some embodiments, the application and the at least one other application are launched by different entities.

It shall be understood that different aspects of the present disclosure can be appreciated individually, collectively, or in combination with each other. Various aspects of the disclosure described herein may be applied to any of the particular applications set forth below. Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF THE DRAWINGS

The technical features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of the following.

FIG. 3D illustrates a perspective view of a wireless platform having a reusable portion coupled to a disposable portion. FIG. 3E illustrate a top view of FIG. 3D. FIG. 3F illustrates a wireless platform in which the reusable portion and disposable portion are in a decoupled state. FIG. 3G illustrates electrical connects integrated in the disposable portion of the wireless platform.

DETAILED DESCRIPTION

While various embodiments are shown and described herein, it will be obvious to those skilled in the art that such embodiments are provided by way of example only. Numerous variations, changes, and substitutions may occur to those skilled in the art without departing from devices, systems and methods disclosed herein. It should be understood that various alternatives to the embodiments described herein may be employed.

Unless otherwise defined, all technical terms used herein have the same meaning as commonly understood by one of ordinary skill in the art to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

Patches

Figure 1A:
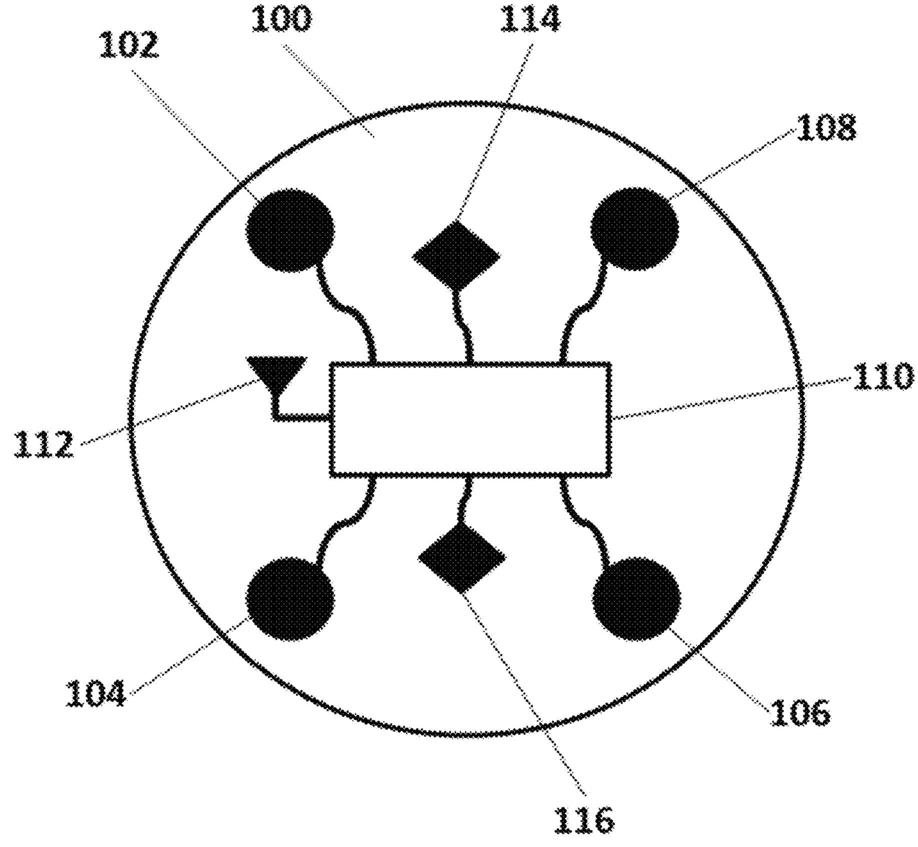
FIG. 1A illustrates an example of a patch.
Figure 1B:
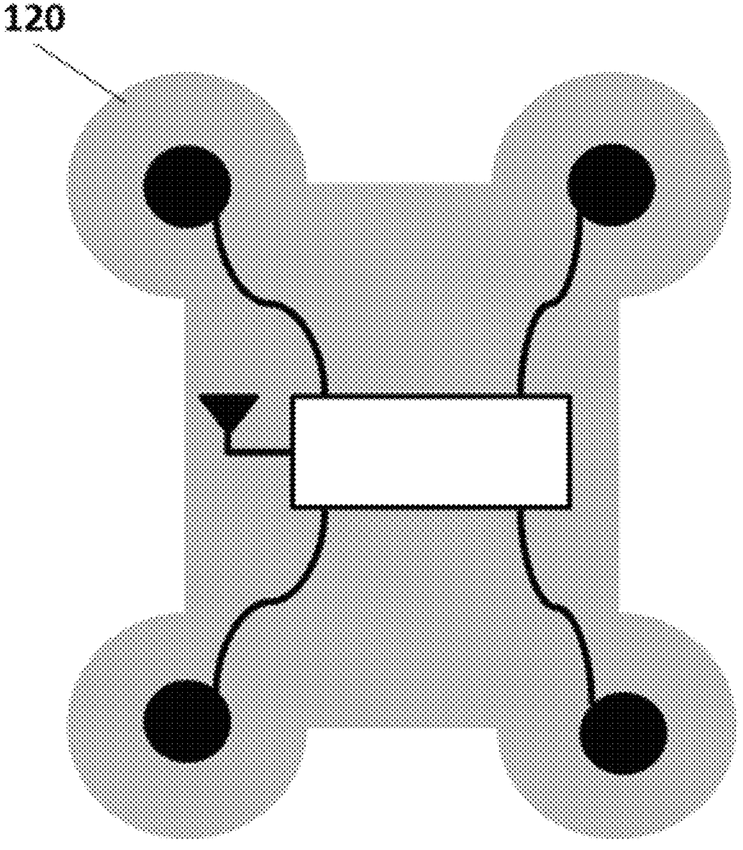
FIG. 1B illustrates an example of a patch having a different base shape than FIG. 1A.

A wireless platform of the present disclosure can comprise a patch with integrated sensors and a communication interface. The patch may be compact. The patch may be configured for adhering to, or otherwise coupling to, a skin of a subject or a clothing worn by the subject. FIGS. 1A-1B illustrate examples of patches.

A patch may be designed for monitoring physiological data. For example, physiological data can include data related to cardiac functionality, respiratory functionality, pulmonary comorbidities, and positional data. Examples of physiological data include, but not limited to, heart rate, cardiac rhythms, respiration, blood oxygenation, body temperature, conductivity, impedance, resistance, motion, orientation, position, synaptic signals, neural signals, voice signals, vision or optical signals, electrocardiogramalectroatriography, electroventriculography, intracardiac electrogram, electroencephalography, electrocorticography, electromyography, electrooculography, electroretinography, electronystagmography, electroolfactography, electroantennography, electrocochleography, electrogastrography, electrogastroenterography, electroglottography, electropalatography, electroarteriography, electroblepharography, electrodermography, electrohysterography, electroneuronography, electropneumography, electrospinography, and electrovomerography.

Referring to FIG. 1A, a patch may comprise a base 100. A base 100 may comprise a flexible substrate. Alternatively, the base 100 may comprise a substantially rigid substrate. Materials of a base 100 may comprise a plastic material, an elastomeric material, and/or a silicone material. The base may be used for holding electrodes and/or electronic components. In some instances, a surface of the base may be designed to contact with a user at a forehead, an arm, a chest, a leg, and a finger. Alternatively or in addition, a surface of the base may be designed to contact another layer, such as an adhesive layer for contacting the user. Alternatively or in addition, a surface of the base may be designed to contact or interface a cover layer, such as a protective cover of the base configured for protecting the base. Alternatively or in addition, a surface of the base may be designed to contact a body interface layer configured for coupling the base to the user. In some instances, a first surface of the base may comprise one or more electronics and a second surface of the base may be configured to interface a user or a layer configured to interface the user.

The base may be of any shape, size, or form. For example, FIG. 1A illustrates a generally circularly formed base. FIG. 1B illustrates another example shape for the base. The patch may be in a small size. For example, the patch may comprise a maximum dimension equal to or smaller than about 5 centimeters (cm), 6 cm, 7 cm, 8 cm, 9 cm, 10 cm, 11 cm, 12 cm, 13 cm, 14 cm, 15 cm, 16 cm, 17 cm, 18 cm, 19 cm, or 20 cm. Alternatively, the patch may be greater than about 20 cm. The thickness of a patch may be equal or less than about 0.1 cm, 0.2 cm, 0.3 cm, 0.4 cm, 0.5 cm, 0.6 cm, 0.7 cm, 0.8 cm, 0.9 cm, 1 cm, 2 cm, 3 cm, 4 cm, 5 cm, 6 cm, 7 cm, or 8 cm. Alternatively, the patch may have a thickness greater than about 8 cm. A patch may have a volume equal to or smaller than about 5 $cm^3$, 10 $cm^3$, 15 $cm^3$, 20 $cm^3$, 25 $cm^3$, 30 $cm^3$, 35 $cm^3$, 40 $cm^3$, 45 $cm^3$, 50 $cm^3$, 60 $cm^3$, 70 $cm^3$, 80 $cm^3$, 90 $cm^3$, or 100 $cm^3$. Alternatively, the patch may have a volume greater than about 100 $cm^3$.

The mass of the patch may be equal or less than about 1 gram, 2 grams, 3 grams, 4 grams, 5 grams, 6 grams, 7 grams, 8 grams, 9 grams, 10 grams, 11 grams, 12 grams, 13 gram, 14 grams, 15 grams, 16 grams, 17 grams, 18 grams, 19 grams, 20 grams, 21 gram, 22 grams, 23 grams, 24 grams, 25 grams, 26 grams, 27 grams, 28 grams, 29 grams, 30 grams, 31 gram, 32 grams, 33 grams, 34 grams, 35 grams, 36 grams, 37 grams, 38 grams, 39 grams, 40 grams, 41 gram, 42 grams, 43 grams, 44 grams, 45 grams, 46 grams, 47 grams, 48 grams, 49 grams, 50 grams, 60 grams, 70 grams, 80 grams, 90 grams, 100 grams, 110 grams, 120 grams, 130 grams, 140 grams, 150 grams, 160 grams, 170 grams, 180 grams, 190 grams, or 200 grams. Alternatively, the patch may have a mass greater than about 200 grams.

A patch may comprise one or more sensors 114, 116, the one or more sensors configured to monitor data (e.g., physiological, positional, etc.) from the user. For example, the number of electrodes may be 1, 2, 3, 4, 5, 6, 7, 8, 9, 10, 11, 12, 13, 14, 15, 16, 17, 18, 19, 20 or more than 20. In the example illustrated in FIG. 1A, four electrodes (102, 104, 106, and 108) may be operably coupled to the base 100. The one or more sensors may each be a different type of sensor. Alternatively, the one or more sensors may comprise duplicate types of sensors (e.g., two temperature sensors, etc.). Sensors of the present disclosure can include, but is not limited to, electrocardiagraphy (ECG) (e.g., multilead ECG), tissue impedance, heart rate, heart rate variation, respiration (e.g., respiration rate and pattern), pulse oximetry (e.g., to detect peripheral capillary oxygen saturation (SpO2)), temperature, accelerometer (e.g., 3-axis), body position and motion, gyroscope, hydration, heart sound, cameras or other optical sensors, microphones or other auditory sensors, and the like.

A patch may comprise an electronic module 110 in communication with the one or more electrodes and one or more sensors. The electronic module may be configured to receive the monitored data from the one or more electrodes and the one or more sensors. The electronic module may be operatively coupled to a wireless transmission mechanism, such as an antenna 112.

In some embodiments, a patch can comprise at least four electrodes comprising at least a right arm (RA, 108), left arm (LA, 102), right leg (RL, 106), and left leg (LL, 104) electrodes. A patch may comprise four or more electrodes configured to gather information sufficient to generate at least three limb leads.

In some instances, the patch and components (e.g., electrodes, sensors, etc.) therein may be configured such that an orientation and placement of patch generates meaningful or high quality data. High quality data as used herein may refer to precise, accurate, interpretable, and/or reproducible data. A single patch of the present disclosure may be sufficient to collect high quality data. A placement of the patch on the human body may be of importance for obtaining a high quality data. For example, high quality data may be obtained when the patch is placed near the upper left chest or at a center of the chest. A patch placed near a center of the chest may be centered over the sternum. A patch placed near a center of the chest may be centered over the sternum and no lower than the xiphoid process.

An orientation of the patch may be of importance for obtaining high quality data. For example, when the patch is placed near the upper left chest, electrodes arranged in a normal orientation (e.g., relative to a longitudinal axis of the user) may enable acquisition of high quality data. A normal orientation as used herein may refer to an arrangement of electrodes wherein electrodes are arranged in a substantially rectangular shape relative to a longitudinal axis of the user. Electrodes arranged in a normal orientation may have a virtual line going through a LA electrode and a RA electrode, which is substantially perpendicular to a longitudinal axis of the user. Electrodes arranged in a normal orientation may have a virtual line going through a LL electrode and a RL electrode, which is substantially perpendicular to a longitudinal axis of the user. Electrodes arranged in a normal orientation may have a virtual line going through a LA and a LL electrode, which is substantially parallel to a longitudinal axis of the user. Electrodes arranged in a normal orientation may have a virtual line going through a RA and a RL electrode, which is substantially parallel to a longitudinal axis of the user. Such configuration of electrodes enables acquisition of high quality data when the patch is placed near the upper left chest. Such configuration of electrodes may enable acquisition of high quality data when the patch is placed near a center of the chest.

In some instances, a different orientation of the patch may be preferred relative to a longitudinal axis of the user. For example, electrodes arranged in a tilted orientation (e.g., relative to a longitudinal axis of the user) may enable acquisition of high quality data. A tilted orientation as used herein may refer to an arrangement of electrodes that is rotated about 15°, 30°, 45°, 60°, 75°, 90°, 120°, 150°, 180° or more clockwise from the normal orientation. A tilted orientation as used herein may refer to an arrangement of electrodes that is rotated about 15°, 30°, 45°, 60°, 75°, 90°, 120°, 150°, 180° or less clockwise from the normal orientation. A tilted orientation as used herein may refer to an arrangement of electrodes that is rotated about 15°, 30°, 45°, 60°, 75°, 90°, 120°, 150°, 180° or more counterclockwise from the normal orientation. A tilted orientation as used herein may refer to an arrangement of electrodes that is rotated about 15°, 30°, 45°, 60°, 75°, 90°, 120°, 150°, 180° or less counterclockwise from the normal orientation. A tilted orientation as used herein may refer to an arrangement of electrodes that is rotated 15°, 30°, 45°, 60°, 75°, 90°, 120°, 150°, or 180° clockwise or counterclockwise from the normal orientation. In some instances, a tilted orientation of electrodes may be arranged in a diamond shape relative to a longitudinal axis of the user. Electrodes arranged in a tilted orientation may have a virtual line going through a LA electrode and a RL electrode be substantially parallel to a longitudinal axis of the user. Electrodes arranged in a tilted orientation may have a virtual line going through a LL and RA electrode be substantially perpendicular to a longitudinal axis of the user. Electrodes arranged in a tilted orientation may have a virtual line going through a LL electrode and a RA electrode be substantially parallel to a longitudinal axis of the user. Electrodes arranged in a tilted orientation may have a virtual line going through a LA and RL electrode be substantially perpendicular to a longitudinal axis of the user.

Patches, and/or associated software thereof, of the present disclosure may be configured to generate, and/or be capable of generating, clinical grade data or medical grade data. For example, data generated by the patches may meet the requirements of one or more accepted clinical or medical standards, models, formats, terminologies, and/or guidelines. In some instances, the standards may include different types of standards, such as measurement standards (e.g., molecular biomarkers, patient-reported outcomes, observer-reported outcomes, clinician-reported outcomes, etc.), methods standards (e.g., disease models, in vitro models, clinical trial simulation tools, etc.), and data standards (e.g., clinical data standards for certain therapeutic areas, etc.). Such standards may be created, accredited, or supported by one or more entities or consortiums, such as the Clinical Data Interchange Standards Consortiums (CDISC), Critical Path Institute (C-Path), Coalition for Accelerating Standards and therapies (CFAST), and Food and Drug Administration (FDA).

In some instances, different requirements may be associated with different therapeutic areas (e.g., cardiovascular, asthma, diabetes, pain, etc.) to qualify as clinical grade data. The patch, and/or associated software thereof, may be configured to generate clinical grade data in one or more different therapeutic areas. In some instances, the patch, and/or associated software thereof, may satisfy requirements presented by one or more open standards (e.g., CDISC Study Data Tabulation Model (SD™) standards, Fast Healthcare Interoperability Resources (FHIR) standards, Institute of Electrical and Electronics Engineers (IEEE) standards, etc.) for clinical grade data. Alternatively or in addition, the patch, and/or associated software thereof, may satisfy requirements presented by one or more guidelines (e.g., Continua Design Guidelines). Alternatively or in addition, the patch, and/or associated software thereof, may satisfy requirements presented by one or more regulatory entities. In some instances, the patches, and/or associated software thereof, may be configured to acquire, and/or be capable of acquiring, data using an acquisition method or procedure (e.g., duration, placement of sensors, orientation of sensors, types of sensors, etc.) that satisfies one or more accepted clinical or medical standards or guidelines.

Sensor Customization

Figure 1C:
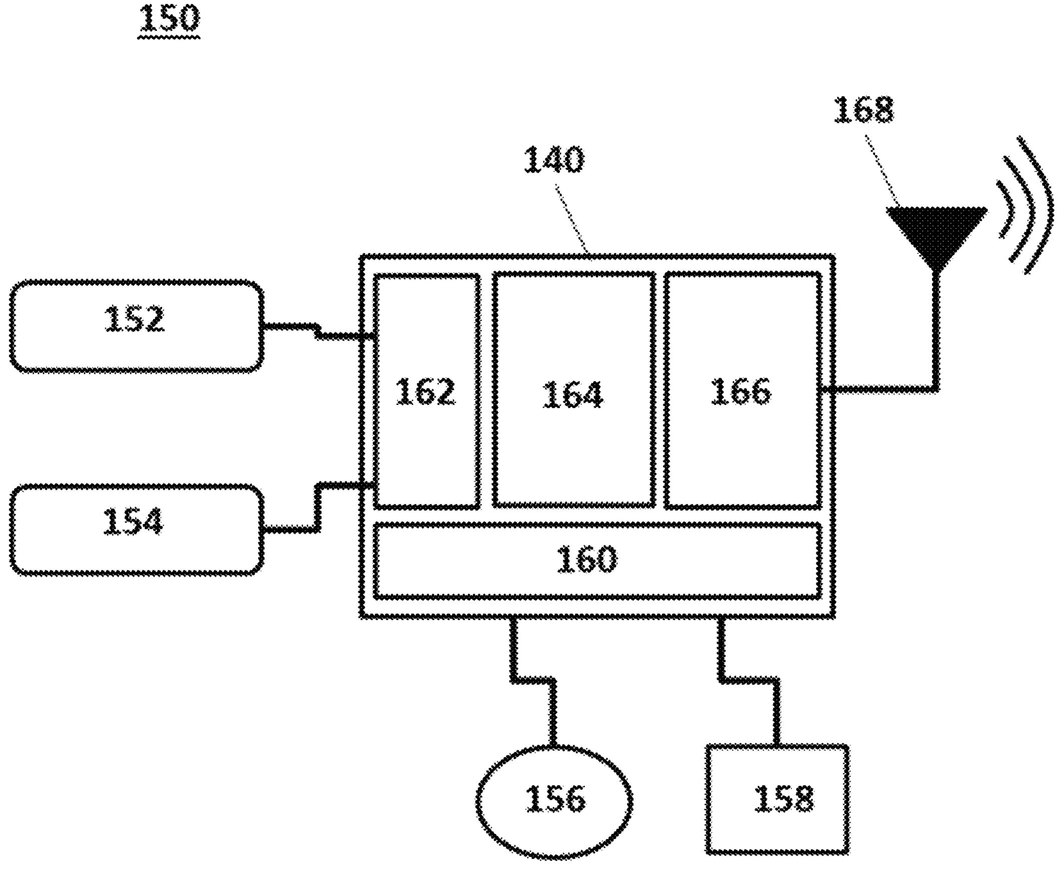
FIG. 1C illustrates an example schematic of a wireless platform.

FIG. 1C illustrates an example schematic of a wireless platform. The wireless platform 150 may comprise the patch described with respect to FIGS. 1A-1B. The patch may be a medical patch. The patch may be capable of performing clinical grade assessments.

The wireless platform 150 may comprise one or more electrodes 152, optionally one or more additional sensors 154, a power storage medium 156, a data storage medium 158, an electronic module 140, and a wireless transmission mechanism 168. The one or more electrodes 152 and the one or more additional sensors 154 may correspond to the one or more electrodes and the one or more sensors described with respect to FIGS. 1A-1B. The sensors may include clinical grade sensors. The wireless platform may be configured to allow clinically-approved placement of the sensors on the subject.

The electronic module 140 may comprise a multi-chip module or application-specific integrated circuit (ASIC) to integrate most of the needed functions into a single module. The ASIC can be a single chip device. In some embodiments, additional components can be added to the ASIC as needed. The electronic module may comprise, or otherwise be electrically coupled to, one or more of the following: one or more of: sensor interface 162, processing unit 164, and wireless communication interface 166. Optionally, the electronic module may comprise one or more optional units 160. For example, the optional units can include, but is not limited to the following: instrumentation amplifiers for ECG and/or respiration signals, signal generation units for impedance variation measurement, right leg driver circuits, antennae, transimpedance amplifiers with LED driver circuits for SpO2, micro-processors, FLASH memory, LED indicators, voltage and temperature sensors, power management units, and defibrillation (or voltage surge) protection circuits with resistors and clamping diodes. The electronic module may comprise other electronic components, such as resistors, capacitors, transcoders, and connectors, to facilitate electrical connection. Alternatively or in addition, the aforementioned components may be located elsewhere on the patch and the electronic module may be in communication with the additional components.

The electronic module 140 may comprise a wireless communication interface 166. The wireless communication interface may comprise one or more of the following: a near range communication mechanism, a short range communication mechanism, and/or a long range communication mechanism. A wireless communication unit may operate on one or more of the following protocols: a Bluetooth protocol, a Wi-Fi protocol, an ultra-wide band (UWB) protocol, and a narrowband protocol. The wireless communication interface may comprise one or more radio transmitters, receivers, and/or transceivers. The radio may enable the patch to communicate with other devices through a wireless link. The radio may be configured to wirelessly transmit and/or receive data. The radio may be configured to wirelessly transmit data to external devices and/or receive data from the external devices.

The radio may be a single-mode, dual-mode, triple-mode, or quad-mode radio. The radio may utilize any known bandwidth, e.g., narrowband, wideband, ultra-wideband, broadband, etc. The radio may communicate through Wi-Fi, Bluetooth, wireless sub, and the like. In some instances, the radio may be a triple-mode hybrid radio. The triple-mode hybrid radio may utilize Wi-Fi, Medical band, and/or ultra-wideband bandwidths. The triple-mode hybrid radio may seamlessly transition between the three modes to maintain link integrity. The triple-mode hybrid radio may select a lowest power option when more than one option is available. Alternatively, the radio may be a single-mode or dual-mode radio. For example, the single-mode radio may utilize Wi-Fi. For example, the single-mode radio may utilize Medical band bandwidths. For example, the single-mode radio may utilize ultra-wideband bandwidths. In some instances, the wireless communication interface may comprise at least one narrowband radio transmitter, receiver, and/or transceiver, and at least one ultrawideband radio transmitter, receiver, and/or transceiver. The wireless communication interface may be operably coupled to one or more antennae, such as wireless transmission mechanism 168 (e.g., one or more antennae).

The electronic module 140 may comprise a sensor interface 162. The sensor interface 162 may be operatively coupled to the one or more electrodes 152 and the optional one or more additional sensors 154. In some instances, each electrode and/or sensor may be individually addressable by the sensor interface. Alternatively or in addition, a subset of electrodes and/or sensors may be addressable collectively.

The electronic module 140 may comprise a processing unit 164. In some instances, the processing unit 164 may be communicatively coupled to the sensor interface 162 and the wireless communication interface 166. The processing unit 164 can be further communicatively coupled to other electrical components, such as the power storage medium 156 (e.g., to receive, distribute, and/or manage power, etc.) and the data storage medium 158 (e.g., to coordinate and store application instructions and data, to coordinate and store sensor data, to coordinate and store programmable instructions of one or more processors, etc.). The power storage medium 156 and the data storage medium 158, while illustrated as external to the electronic module 140, may in some cases be integrated in the electronic module 140. The processing unit 164 can be further communicatively coupled to all or parts of the one or more optional units 160, such as a power management unit.

The processing unit 164 may comprise one or more processors and a memory operably coupled to the one or more processors to execute systems and methods of the present disclosure. The processing unit 164 may be configured to communicate with the one or more electrodes 152 and/or the optional one or more sensors 154 via the sensor interface 162, such as to receive sensor data from and/or transmit instructions to the sensors (or sensor components). The processing unit 164 may be configured to communicate with one or more external devices (not illustrated) via the wireless communication interface 166, such as to receive application instructions from and/or transmit sensor data to the one or more external devices.

The processing unit 164 may coordinate communication between an application being executed (or implemented) on an external device and a selected combination of one or more sensors. As described elsewhere herein, different sensors in the plurality of sensors may be configured to collect different types of data from the subject. Different applications executed on the one or more external devices can be configured to activate, transfer data to, receive data from, and/or otherwise utilize data from different combinations of sensors (e.g., 152, 154) integrated in the wireless platform 150. The wireless platform, and/or a selected combination of sensors therein, can be activated by an external device via one or more different applications. Different applications may utilize the different combinations of sensors of wireless platform 150 to achieve one or more application-specific objectives. Such objectives can include, for example, the monitoring, tracking, and/or detection of one or more activities.

For example, the objectives can include, but are not limited to, cardiac care, monitoring and detecting cardiac electrical activity, monitoring and detecting cardiac rhythm assessment, monitoring and detecting mechanical heart conditions, monitoring and detecting respiration, monitoring and detecting lead-off states, monitoring skin temperature, monitoring blood oxygen levels, monitoring and detecting sleep apnea, monitoring and detecting snoring, monitoring and detecting sleep positions, monitoring and detecting sleep patterns, monitoring and detecting sleep REM activity, monitoring athlete fitness state, monitoring and detecting fitness activities (e.g., running, walking, rowing, planking, etc.), monitoring and detecting activity intensities and patterns, infant monitoring, pet monitoring, senior living, monitoring gait, monitoring and detecting mental stress, monitoring and detecting emotional states, monitoring and detecting falls, monitoring and detecting positional state, and monitoring and detecting other motion, among other objectives described herein.

Provided herein are examples of combinations of one or more sensors to achieve specific objectives. An application may utilize a multi-lead ECG sensor to monitor cardiac electrical activity and/or rhythm assessment. An application may utilize a tissue impedance sensor to monitor respiration and perform lead-off detection. An application may utilize a temperature sensor to monitor skin temperature. An application may utilize a pulse oximetry sensor (SpO2) to monitor blood oxygenation levels. An application may utilize an accelerometer(S) as a heart sound sensor to quantify mechanical heart conditions. An application may utilize an accelerometer (R) as a respiration rate and pattern sensor to detect snoring and sleep apnea-type issues. An application may utilize a microphone to detect and monitor cardiac sounds.

Examples for applications directed to sleep health objectives are provided. An application may utilize an accelerometer (M) as a body position and motion sensor to detect activity intensities and patterns as well as sleep positions and other bodily positions. An application may utilize an ECG sensor and accelerometer (R) for analyzing sleep quality and restfulness. An application may utilize an ECG sensor, accelerometer (R), and accelerometer (M) for analyzing sleep position correlation. An application may utilize an impedance sensor and accelerometer (R) for analyzing respiration patterns. An application may utilize an accelerometer(S) for detecting snoring. An application may utilize an impedance sensor and accelerometer(S) for detecting sleep apnea. An application may utilize an ECG sensor, impedance sensor, accelerometer (R), and pulse oximetry sensor (SpO2) for clinical sleep assessment. Beneficially, different combinations of the sensors may achieve objectives at each of a personal screening level (e.g., sleep quality/restfulness, sleep position correlation, respiration pattern) a personal testing level (e.g., snoring detection, sleep apnea detection), and a clinical testing level (e.g., clinical sleep assessment).

Examples for applications directed to cardiac health objectives are provided. An application may utilize an ECG sensor, impedance sensor, and temperature sensor to monitor vital signs including heart rate, respiration rate, and temperature. An application may utilize an ECG sensor and an impedance sensor to monitor resting cardiac wellness. An application may utilize an ECG sensor, an accelerometer (M), and an accelerometer (R) to monitor active cardiac wellness. An application may utilize an ECG sensor and an accelerometer(S) to monitor mechanical heart health. An application may utilize an ECG sensor, an impedance sensor, and an accelerometer(S) for a clinical heart assessment. Beneficially, different combinations of the sensors may achieve objectives at each of a personal screening level (e.g., vital signs monitoring, resting cardiac wellness) a personal testing level (e.g., active cardiac wellness, mechanical heart health), and a clinical testing level (e.g., clinical heart assessment). An example application-to-sensors correlation chart, Table 1, is provided below:

TABLE 1

Application-to-sensors correlation chart

| Application | Sensors | | | | | | | |
|---|---|---|---|---|---|---|---|---|
| | ECG | Heart Rate | Respiration | SpO2 | Temperature | Heart Sound | Motion | . . . |
| Application 1 | | | | | ✓ | | | |
| Application 2 | ✓ | | | | | | ✓ | |
| Application 3 | | | ✓ | | | | ✓ | |
| Application 4 | ✓ | | ✓ | ✓ | | | ✓ | |
| . . . | | | | | | | | |

The available combinations of one or more sensors by an application are not limited to the above specific examples. For example, an application can select and utilize any combination of the different types of sensors described in this application, including variations involving duplicate types of sensors (e.g., three temperature sensors and one impedance sensor). An application can select and utilize any combination of sensors that are integrable in the wireless platform 150 described herein.

An application may comprise client software. An application may be executable (or implemented) by a computing device (e.g., one or more external devices). In some embodiments, the client software (i.e., software applications installed on the external devices) may be available as downloadable or native mobile applications for various types of mobile devices. Alternatively, the software may not be a mobile application. Alternatively or in addition, the client software can be implemented in a combination of one or more programming languages and markup languages for execution by various web browsers. For example, the client software can be executed in web browsers that support JavaScript and HTML rendering, such as Chrome, Mozilla Firefox, Internet Explorer, Safari, and any other compatible web browsers. In some instances, an application may be natively designed by the manufacturer of the wireless platform described herein. In some instances, an application may be designed by any user, individual, entity, operator, clinician, or others related to or using the wireless platform. For example, two different users (e.g., different entities) may create two different applications that are compatible for use with the same wireless platform. In some instances, such applications may be collected in a library of applications for use with the wireless platform. An application may contain metadata regarding compatible wireless platforms (e.g., having minimum sensor requirements). In some instances, various embodiments of a client software application may be compiled for various devices, across multiple platforms, and may be optimized for their respective native platforms. In some cases, third-party user interfaces or APIs may be integrated to application and integrated in the front-end user interface (e.g., within a graphical user interface). The third-party user interfaces may be hosted by a third party server.

In some instances, an application may be defined by at least: a selection of one or more sensors, and amount or duration of data required from the one or more sensors. In some instances, an application may comprise instructions for optimal or preferred patch placement and/or orientation, such as with respect to a reference point in the body (e.g., center of chest) and/or a reference orientation, respectively. For example, an application that utilizes a temperature sensor in the patch may comprise instructions for placement of the patch in a desired target location for temperature measurement. In another example, an application that tracks motion may prefer placement of the patch at or near the center of the chest to filter out background movement (e.g., from the limbs) and reduce background noise.

In some instances, all sensors in a wireless platform 150 may be in operation, such as to collect data. Upon pairing with an external device and/or an application utilizing a selected combination of one or more sensors, the wireless platform 150 may transmit all collected data to the application, and the application may utilize a subset of the collected data from the selected combination of one or more sensors. Alternatively, upon pairing with the external device and/or the application utilizing a selected combination of one or more sensors, the wireless platform 150 may transmit only a subset of the collected data from the selected combination of one or more sensors. Alternatively, all sensors in a wireless platform 150 may not be in operation, and upon pairing with the external device and/or the application utilizing a selected combination of one or more sensors, the wireless platform 150 may activate the selected combination of one or more sensors or only collect data from the selected combination of one or more sensors, and transmit the subset of the collected data from the selected combination of one or more sensors. Alternatively, all sensors in a wireless platform 150 may be in operation, and upon pairing with the external device and/or the application utilizing a selected combination of one or more sensors, the wireless platform 150 may deactivate the non-selected sensors, and transmit the collected data from the selected combination of one or more sensors.

In some instances, the wireless platform 150 and the external device may have a one-way communication, such that the external device is only transmitting instructions to the wireless platform 150 (e.g., for sensor activation or deactivation) or only receiving sensor data from the wireless platform. In other instances, the wireless platform 150 and the external device may have a two-way communication, such that the external device can both transmitting instructions to the wireless platform 150 (e.g., for sensor activation or deactivation) and also receive sensor data from the wireless platform.

Figure 2A:
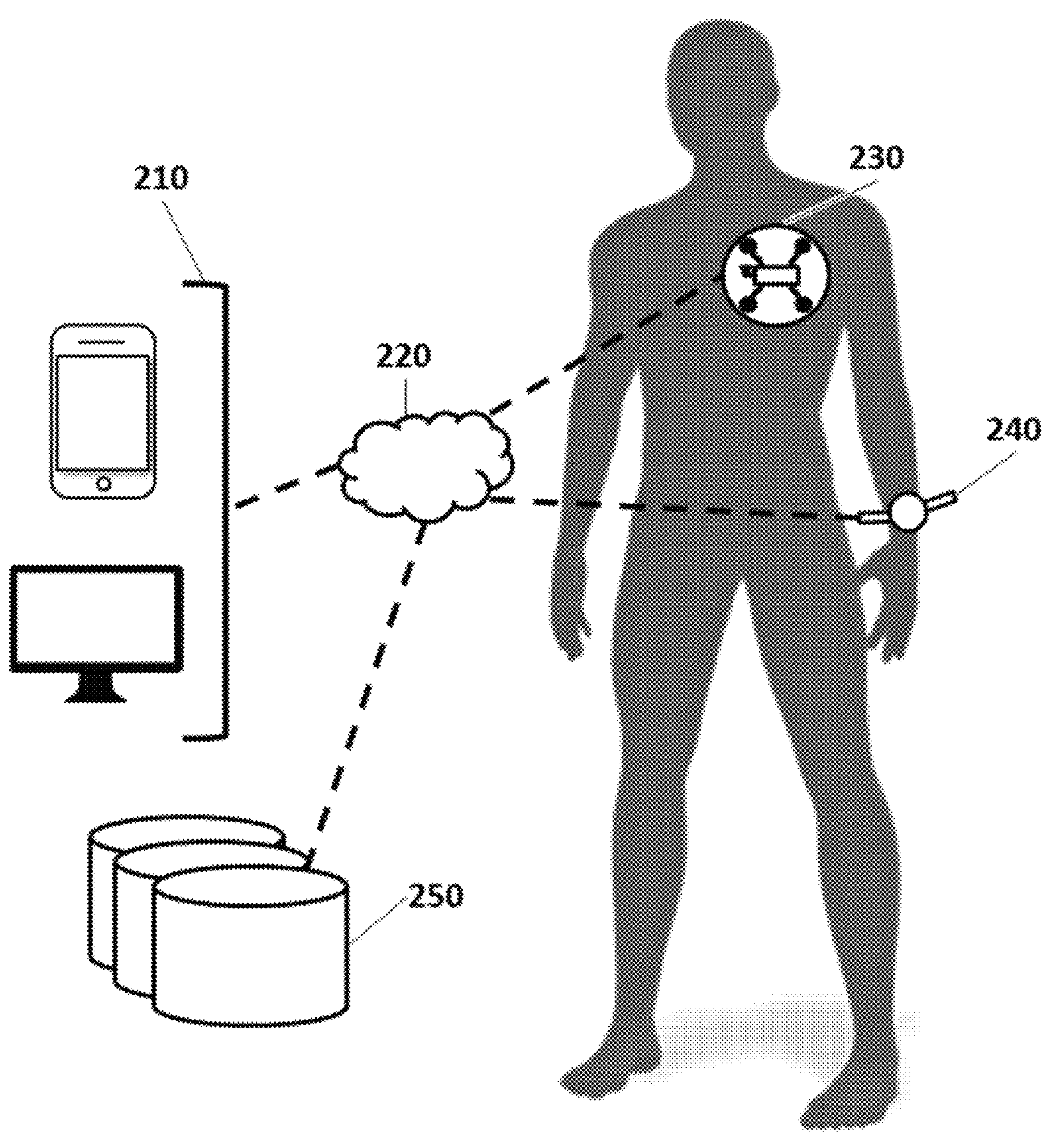
FIGS. 2A-2C illustrates a communication schematic between an application and a wireless platform.

FIG. 2A illustrates a communication schematic between an application and a wireless platform. One or more applications executed on one or more external devices 210 may communicate with a wireless platform 230, directly and/or via network 220. Optionally the one or more external devices 210 and/or the wireless platform 230 may communicate with a wearable device 240, directly and/or via network 220. Optionally the one or more external devices 210, wireless platform 230, and/or the wireless device 240 may communicate with one or more servers 250, directly and/or via network 220.

Each of the components (e.g., wireless platform, external devices, wearable device, servers, and the like) may be operatively connected to one another via one or more networks (e.g., network 220) or any type of communication links that allows transmission of data from one component to another. For example, the respective hardware components may comprise network adaptors allowing unidirectional and/or bidirectional communication with one or more networks.

Figure 2B:
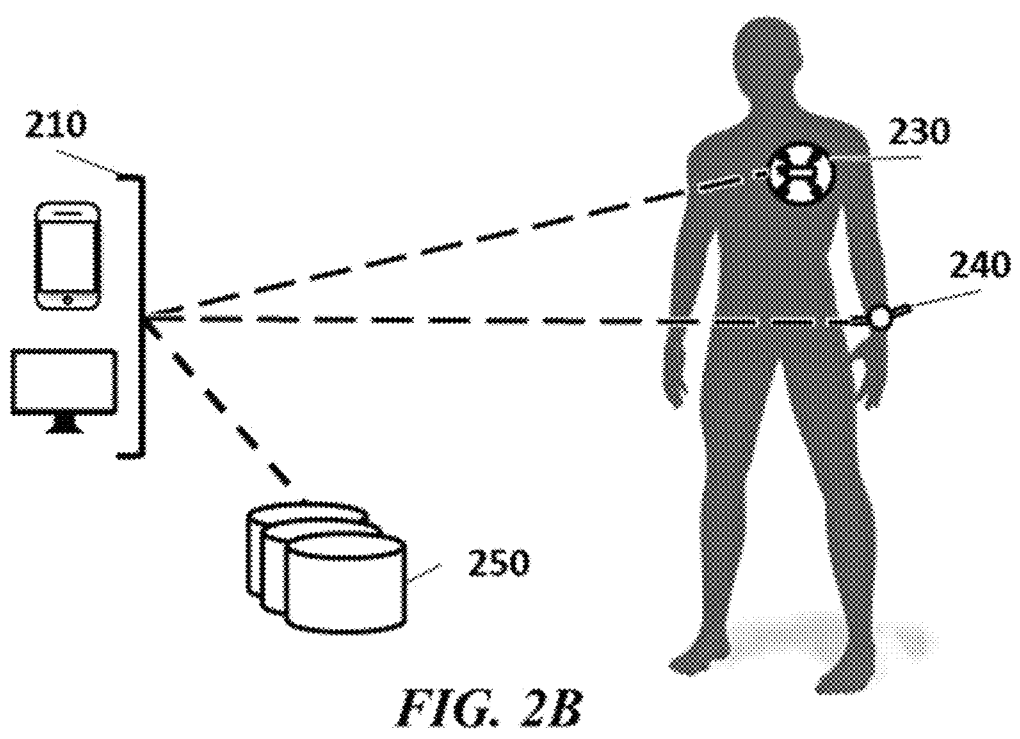

FIG. 2B illustrates another communication schematic between an application and a wireless platform. One or more applications executed on one or more external devices 210 may communicate with a wireless platform 230 directly. Optionally the one or more external devices may communicate with a wearable device 240 directly. Optionally the one or more external devices 210 may communicate with one or more servers 250. Each of the components (e.g., wireless platform, external devices, wearable device, servers, and the like) may be operatively connected to one another directly or via one or more networks (e.g., network 220) or any type of communication links that allows transmission of data from one component to another. Examples of communicative links include, for example, Bluetooth, Near Field Communication (NFC), Wi-Fi, Ethernet, and the like. For example, the respective hardware components may comprise network adaptors allowing unidirectional and/or bidirectional communication with one or more networks.

Figure 2C:
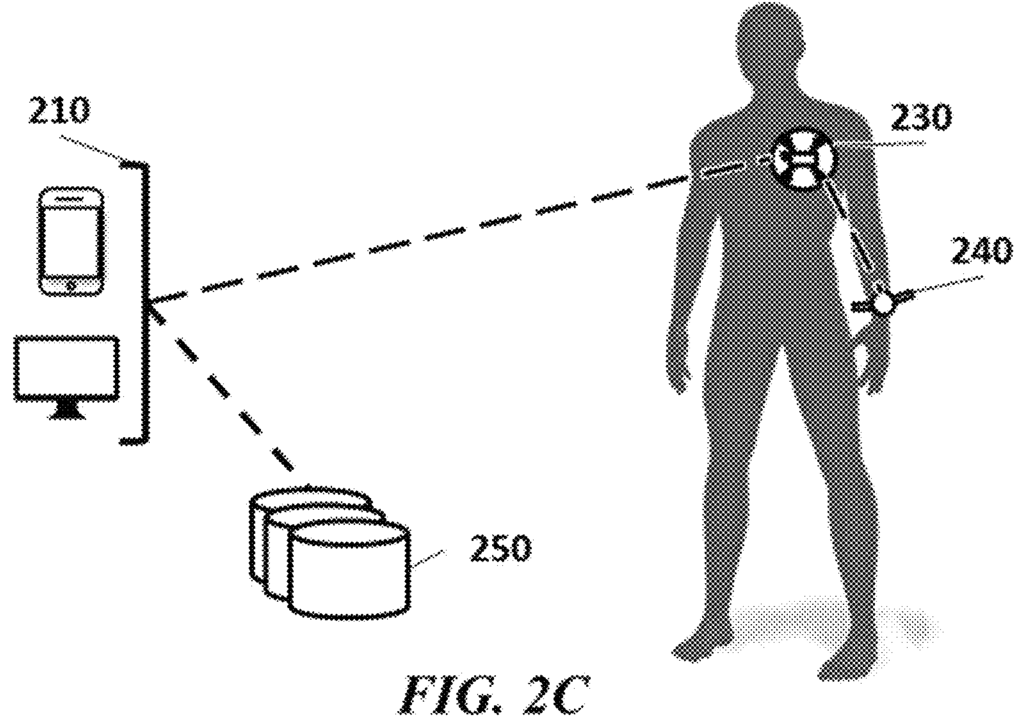

FIG. 2C illustrates another communication schematic between an application and a wireless platform. One or more applications executed on one or more external devices 210 may communicate with a wireless platform 230 directly. Optionally the wireless platform 230 may communicate with a wearable device 240 directly. Optionally the one or more external devices 210 may communicate with one or more servers 250. Each of the components (e.g., wireless platform, external devices, wearable device, servers, and the like) may be operatively connected to one another directly or via one or more networks (e.g., network 220) or any type of communication links that allows transmission of data from one component to another. Examples of communicative links include, for example, Bluetooth, Near Field Communication (NFC), Wi-Fi, Ethernet, and the like. For example, the respective hardware components may comprise network adaptors allowing unidirectional and/or bidirectional communication with one or more networks.

The wireless platform 230 may correspond to the wireless platform 150 described elsewhere herein (e.g., with respect to FIG. 1C). While one wireless platform 230 is illustrated in FIG. 2, any number of wireless platforms may be in communication with each other and/or other components of FIG. 2.

An external device of the one or more external devices 210 may be a computing device configured to perform one or more operations consistent with the disclosed embodiments. Examples of computing devices may include, but are not limited to, mobile devices, smartphones/cellphones, tablets, personal digital assistants (PDAs), smart wearable devices, smart watches, laptop or notebook computers, desktop computers, media content players, television sets, video gaming station/system, virtual reality systems, augmented reality systems, microphones, or any electronic device configured to enable the user to implement an application associated with the wireless platform 230 or run a command on the application. The computing device may be a handheld object. The computing device may be portable. The computing device may be carried by a human user. The computing device may be a substantially mobile device. The computing device may be a substantially stationary device. In some cases, the computing device may be an electronic device coupled to or located on-board a vehicle. In some cases, the computing device may be located remotely from a human user, and the user can control the computing device using wireless and/or wired communications. The computing device may be a computing device in communication with a wearable device worn by a user. In some cases, the wearable device may be configured to monitor user activities, vital signs (e.g., blood pressure and heart rate vitals) or health conditions of a user, such as via the wireless platform 230 or via independent sensors integrated in the wearable device or otherwise coupled to the wearable device.

The computing device may include a communication unit, which may permit the communications with one or more other components in the network, such as with the wireless platform 230 and/or the wearable device 240. In some instances, the communication unit may include a single communication module, or multiple communication modules. In some instances, the computing device may be capable of interacting with one or more components in the network environment using a single communication link or multiple different types of communication links. The communication unit may include a network adapter.

The computing device may include one or more processors that are capable of executing non-transitory computer readable media that may provide instructions for one or more operations consistent with the disclosed embodiments. The computing device may include one or more memory storage devices comprising non-transitory computer readable media including code, logic, or instructions for performing the one or more operations. As described elsewhere herein, the computing device may interact or otherwise interface with the wireless platform 230 by way of one or more software applications (i.e., client software) running on and/or accessed by the computing device. Software applications and client software are described elsewhere herein.

The wearable device 240 may be a computing device, such as described with respect to the one or more external devices 210.

An application may analyze and/or process sensor data received from the wireless platform 230 to provide one or more outputs via an output interface. The one or more outputs may be associated with the one or more objectives of an application. The one or more outputs may include a representation (e.g., graphical) of raw signals. The one or more outputs may include a representation (e.g., graphical) of processed signals. The one or more outputs may include a representation of data analytics. The one or more outputs may include reference information, for example accessed from a storage (e.g., database), such as from external sources or pre-programmed sources (e.g., reference heart rate for an age group). The one or more outputs may include visual outputs provided on a display, such as a graphical user interface (GUI). For example, the visual outputs can include graphs, charts, tables, time charts, histograms, trends over time, cool diagrams, evaluations, statements, messages, pie charts, or event markers, among other possible visual data outputs. Alternatively or in addition, the one or more outputs may include non-visual outputs provided via other user interface, such auditory outputs (e.g., beeping, etc.), haptic outputs (e.g., vibrations, etc.), olfactory outputs (e.g., dispensing an odor), or other non-visual outputs.

In some instances, the output interface (e.g., display, speaker, actuator, etc.) may be integrated in the one or more external devices 210 running the application. In some instances, the output interface may be otherwise operatively coupled to the one or more external devices, such as via wired or wireless connection. In some instances, the output interface may be integrated in the wearable device 240, or otherwise operatively coupled to the wearable device. In some instances, the one or more outputs may be provided on more than one output interface, such as on both an external device and a wearable device. In some instances, the same outputs may be provided to both the external device and the wearable device. In some instances, different outputs may be provided to both the external device and the wearable device. For example, an output (e.g., summary graph) provided to the wearable device may be less detailed than the output (e.g., detailed graph) provided to the external device, or vice versa, such as to accommodate different capabilities of the respective output interfaces (e.g., different screen sizes).

In some instances, the analytics and/or processing may be performed by the external device executing the application. Alternatively or in addition, the analytics and/or processing may be performed individually or collectively by the wireless platform 230 (e.g., pre-processing sensor data), wearable device 240, and the external device. Alternatively or in addition, the analytics may be performed in coordination with, or independently, by one or more servers 250 in communication with the external device.

A server (e.g., servers 250) may include a web server, a mobile application server, an enterprise server, or any other type of computer server, and can be computer programmed to accept requests (e.g., HTTP, or other protocols that can initiate data transmission) from a computing device (e.g., user device, other servers) and to serve the computing device with requested data. A server may also be a server in a data network (e.g., a cloud computing network). A server may be a unitary server or a distributed server spanning multiple computers or multiple datacenters. The servers may be of various types, such as, for example and without limitation, web server, news server, mail server, message server, advertising server, file server, application server, exchange server, database server, proxy server, another server suitable for performing functions or processes described herein, or any combination thereof. In addition, a server can be a broadcasting facility, such as free-to-air, cable, satellite, and other broadcasting facility, for distributing data. In some instances a server, such as a cloud server, may be associated with and/or in communication with one or more user accounts (accessing or communicating with the cloud server via the one or more external devices 210, for example). In some instances, the server may be associated with a client software (e.g., an application). The server may be configured to dispatch updates to the client software, such as by tracking the implementations of the client software on the one or more external devices 210 and/or communicating with the one or more user accounts.

A server may include various computing components, such as one or more processors, one or more memory devices storing software instructions executed by the processor(s), and data. A server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers.

The application may be in communication with a cloud server to implement cloud-based analytics of sensor data.

The operations described herein may be implemented anywhere in the network. For example, the processing and/or analytics may be implemented in a distributed architecture (e.g., a plurality of devices collectively performing together to implement or otherwise execute the operations) or in a duplicate manner (e.g., a plurality of devices each implementing or otherwise executing the operations as a standalone system). The operations described herein may be implemented using software, hardware, or a combination of software and hardware in one or more of the above-mentioned components in FIG. 2.

Beneficially, the wireless platform provided herein may have sufficient flexibility to accommodate and enable the monitoring of different activities, even those uncontemplated at the time of manufacture of the hardware portion of the wireless platform. Any user, such as individuals, entities, manufacturers, healthcare professionals, medical operators, and others, may design and engineer an application utilizing any combination of a plurality of sensors included in the wireless platform to achieve an objective, including clinical objectives. For example, two different users (e.g., different entities) may create two different applications that are compatible for use with the same wireless platform. Such applications may be created, prior to, simultaneously, or subsequent to manufacture of the hardware portion of the wireless platform. The wireless platform may comprise a processor and/or electronic module capable of controlling the plurality of sensors in the wireless platform to comply with the requirements and instructions of the different applications executed by an external device in communication with the wireless platform via a communication interface of the wireless platform.

FIGS. 3A-3G illustrate a wireless platforms comprising modular portions. In some instances, a wireless platform may comprise at least a disposable portion (or module) and a reusable portion (or module). The disposable portion and the reusable portion may be coupled together. The disposable portion and the reusable portion can be easily decoupled. The disposable portion and the reusable portions may be coupled and decoupled via for example, such as a magnetic snap-on.

Alternatively or in addition, the coupling may be via any type of complementary or one-way fastening mechanism. For example, a first connector in the disposable portion and a second connector in the reusable portion can complete a form-fitting pair. The first connector can comprise a form-fitting male component and the second connector can comprise a form-fitting female component, and/or vice versa. Alternatively or in addition, the two connectors can comprise other types of complementary units or structures (e.g., hook and loop, latches, snap-ons, buttons, nuts and bolts, etc.) that can be fastened together. Alternatively or in addition, the two portions can be fastened using other fastening mechanisms, such as but not limited to staples, slips, clips, clamps, prongs, rings, brads, rubber bands, rivets, grommets, pins, ties, threads (e.g., screws), snaps, velcro, adhesives (e.g., glue), magnets or magnetic fields, tapes, a combination thereof, or any other types of fastening mechanisms. The fastening can be temporary, such as to allow for subsequent unfastening of the parts without damage (e.g., permanent deformation, disfiguration, etc.) to either of the two connectors or with minimal damage. In some instances, one or both of the two portions can be cut into or pierced by the other when the two connectors are fastened together. The fastening can be permanent, such as to allow for subsequent unfastening of the two portions only by damaging at least one of the two portions (e.g., damaging the disposable portion). One of the two connectors, or both, can be temporarily or permanently deformed (e.g., stretched, compressed, etc.) and/or disfigured (e.g., bent, wrinkled, folded, creased, etc.) or otherwise manipulated when fastened to each other or during fastening. In some instances, one or both of the two portions can be cut into or pierced by the other when the two portions are fastened together.

The reusable portion may comprise one or more of the electronic components described elsewhere herein, such as one or more of the electronic module (e.g., 110, 140), one or more sensors (e.g., electrodes 152, optional additional sensors 154), power storage medium (e.g., 156), data storage medium (e.g., 158), wireless transmission mechanism (e.g., 168). In some instances, the reusable portion may comprise all of the electronic components described herein with respect to the patch. The reusable portion may comprise a battery (e.g., rechargeable battery, lithium ion battery, etc.) or other power storage medium (e.g., capacitor, ultracapacitor, supercapacitor, fuel cell, electrochemical cell, solar cell, etc.) that can be rechargeable.

The disposable portion may act as the interface between the reusable portion and a skin of the subject or to a clothing of the subject. The disposable portion may comprise an adhesive mechanism (or other fastening mechanism described herein) to allow coupling of the reusable portion to a skin of the subject or to a clothing of the subject. The disposable portion may comprise one or more conductive electrical connects to conduct electricity between the point of contact with the subject (e.g., skin, clothing) and one or more electronic components (e.g., sensors) of the reusable portion.

Figure 3A:
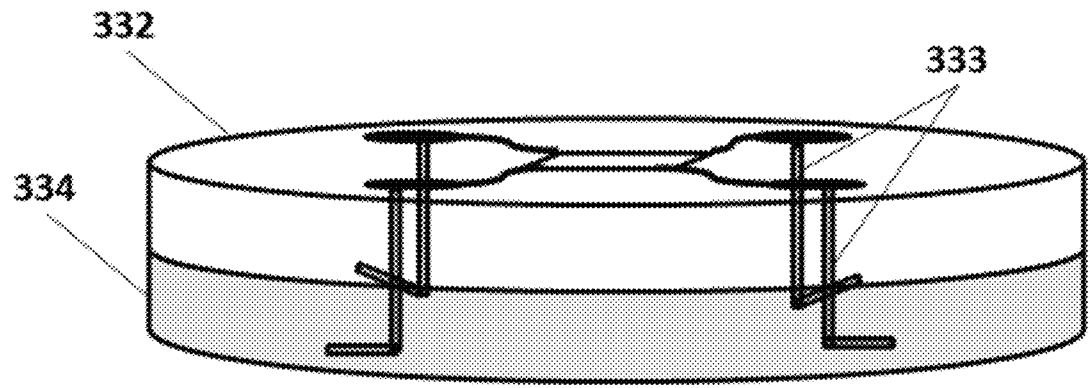
FIG. 3A illustrates one example of a wireless platform having a reusable portion coupled to a disposable portion.

FIG. 3A illustrates one example of a wireless platform having a reusable portion 332 coupled to a disposable portion 334. The reusable portion 332 comprises electronics. The disposable portion 334 can comprise electrical connects 333, such as to electrically connect (or provide better electrical connection between) the sensors in the reusable portion and the point of contact (e.g., skin, clothing or the subject). In this example, the reusable portion and the disposable portion are overlaid such that the reusable portion is adjacent to, disposed above, and contacting the disposable portion.

Figure 3B:
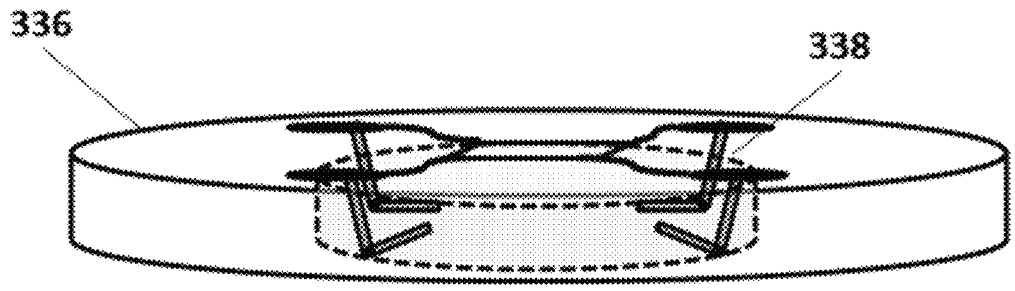
FIG. 3B illustrates another example of a wireless platform having a reusable portion coupled to a disposable portion.

FIG. 3B illustrates another example of a wireless platform having a reusable portion 336 coupled to a disposable portion 338. The reusable portion 336 comprises electronics. The disposable portion 338 can comprise electrical connects, such as to electrically connect (or provide better electrical connection between) the sensors in the reusable portion and the point of contact (e.g., skin, clothing or the subject). In this example, the reusable portion substantially surrounds and the disposable portion which is fitted into an inner region of the reusable portion, such that the reusable portion is adjacent to, disposed around, and contacting the disposable portion.

Figure 3C:
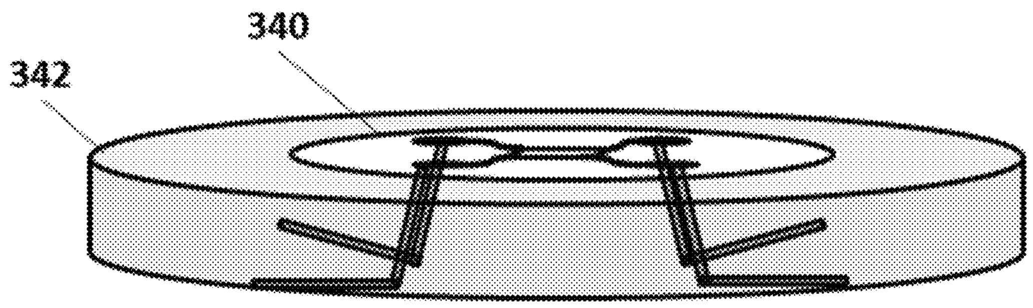
FIG. 3C illustrates another example of a wireless platform having a reusable portion coupled to a disposable portion.

FIG. 3C illustrates another example of a wireless platform having a reusable portion 340 coupled to a disposable portion 342. The reusable portion 340 comprises electronics. The disposable portion 342 can comprise electrical connects, such as to electrically connect (or provide better electrical connection between) the sensors in the reusable portion and the point of contact (e.g., skin, clothing or the subject). In this example, the reusable portion is substantially surrounded by the disposable portion and fits into an inner region of the disposable portion, such that the reusable portion is adjacent to, disposed within, and contacting the disposable portion.

It will be appreciated that the any arrangement of the disposable portion and the reusable portion is allowed, wherein at least a surface of the disposable portion contacts the subject (e.g., the skin or a clothing, etc.) and at least another surface of the disposable portion contacts the reusable portion. The electronics in the reusable portion may have an electrical connection to the subject either directly, or via the disposable portion. The disposable portion and the reusable portion may each have any arbitrary size, shape, and form. In some instances, the disposable portion and the reusable portion may have substantially different sizes, shapes, and/or forms. In some instances, the disposable portion and the reusable portion may have substantially same sizes, shapes, and/or forms.

A method of using the wireless platform may comprise coupling a reusable portion to a disposable portion of the wireless platform, and coupling a surface of the disposable portion to a target location on a subject. The method may further comprise decoupling the wireless platform from the subject. The method may further comprise decoupling the reusable portion and the disposable portion. The method may further comprise disposing the disposable portion. The method may further comprise coupling the reusable portion with another disposable portion, and repeating the above. In some instances, the method may further comprise, between switching out the disposable portions, recharging a power supply of the reusable portion.

FIG. 3D illustrates a perspective view of a wireless platform having a reusable portion 146 coupled to a disposable portion 144. FIG. 3E illustrate a top view of FIG. 3D. FIG. 3F illustrates a wireless platform in which the reusable portion 146 and disposable portion 144 are in a decoupled state. FIG. 3G illustrates electrical connects 148 integrated in the disposable portion 144 of the wireless platform.

Computer Systems

In some examples, the platforms, systems, media, and methods described herein may include a digital processing device, or use of the same. Any computing device described herein may be a digital processing device. In some examples, the digital processing device may include one or more hardware central processing units (CPUs) or general purpose graphics processing units (GPGPUs) that carry out the device's functions. In some examples, the digital processing device may further comprise an operating system configured to perform executable instructions. The digital processing device may be optionally connected a computer network. The digital processing device may be optionally connected to the Internet such that it accesses the World Wide Web. The digital processing device may be optionally connected to a cloud computing infrastructure. The digital processing device may be optionally connected to an intranet. The digital processing device may be optionally connected to a data storage device.

In accordance with the description herein, suitable digital processing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Many smartphones may be suitable for use in the system described herein. Televisions, video players, and digital music players with optional computer network connectivity may be suitable for use in the system described herein. Suitable tablet computers may include those with booklet, slate, and convertible configurations, known to those of skill in the art.

The digital processing device may include an operating system configured to perform executable instructions. The operating system may be, for example, software, including programs and data, which manages the device's hardware and provides services for execution of applications. Suitable server operating systems may include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems may include, by way of non-limiting examples, Microsoft® Windows®, Apple® Mac OS X®, UNIX®, and UNIX-like operating systems such as GNU/Linux®. In some examples, the operating system may be provided by cloud computing. Suitable mobile smart phone operating systems may include, by way of non-limiting examples, Nokia® Symbian OS, Apple® iOS®, Research In Motion® BlackBerry OS®, Google® Android®, Microsoft® Windows Phone® OS, Microsoft Windows Mobile® OS, Linux®, and Palm® WebOS®. Suitable media streaming device operating systems may include, by way of non-limiting examples, Apple TV®, Roku®, Boxee®, Google TV®, Google Chromecast®, Amazon Fire®, and Samsung® HomeSync®. Suitable video game console operating systems may include, by way of non-limiting examples, Sony® PS3®, Sony® PS4®, Microsoft® Xbox 360®, Microsoft Xbox One, Nintendo® Wii®, Nintendo® Wii U®, and Ouya®.

The device may include a storage and/or memory device. The storage and/or memory device may be one or more physical apparatuses used to store data or programs on a temporary or permanent basis. The device may be volatile memory and may require power to maintain stored information. The device may be non-volatile memory and retains stored information when the digital processing device is not powered. The non-volatile memory may comprise flash memory, dynamic random-access memory (DRAM), ferroelectric random access memory (FRAM), phase-change random access memory (PRAM).

The digital processing device may include a display to send visual information to a user. The display may be a cathode ray tube (CRT), a liquid crystal display (LCD), a thin film transistor liquid crystal display (TFT-LCD), an organic light emitting diode (OLED) display, a passive-matrix OLED (PMOLED) or active-matrix OLED (AMOLED) display, a plasma display, and/or a video projector.

The digital processing device may include an input device to receive information from a user. The input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera or other sensor to capture motion or visual input. The input device may be a Kinect, Leap Motion, or the like. The input device may be a combination of devices such as those disclosed herein.

The platforms, systems, media, and methods disclosed herein may include one or more non-transitory computer readable storage media encoded with a program including instructions executable by the operating system of an optionally networked digital processing device. A computer readable storage medium may be a tangible component of a digital processing device. A computer readable storage medium is optionally removable from a digital processing device. A computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein may include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, a computer program may be written in various versions of various languages.

A computer program may include a web application. In light of the disclosure provided herein, a web application may utilize one or more software frameworks and one or more database systems. A web application may be created upon a software framework such as Microsoft® .NET or Ruby on Rails (RoR). A web application may utilize one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). A web application may be written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. A web application may be written to some extent in a database query language such as Structured Query Language (SQL).

A computer program may include a mobile application provided to a mobile digital processing device. The mobile application may be provided to a mobile digital processing device at the time it is manufactured. The mobile application may be provided to a mobile digital processing device via the computer network described herein.

A mobile application may be created, for example, using hardware, languages, and development environments. Mobile applications may be written in various programming languages. Suitable programming languages include, by way of non-limiting examples, C, C++, C#, Objective-C, Java™, Javascript, Pascal, Object Pascal, Python™, Ruby, VB .NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Several commercial forums may be available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

A computer program may include a standalone application, which is a program that is run as an independent computer process, not an add-on to an existing process, e.g., not a plug-in. Standalone applications may be compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program.

The computer program may include a web browser plug-in. In computing, a plug-in may be one or more software components that add specific functionality to a larger software application. Makers of software applications support plug-ins to enable third-party developers to create abilities which extend an application, to support easily adding new features, and to reduce the size of an application. When supported, plug-ins may enable customizing the functionality of a software application. For example, plug-ins are commonly used in web browsers to play video, generate interactivity, scan for viruses, and display particular file types. Web browser plug-ins include, without limitation, Adobe® Flash® Player, Microsoft® Silverlight®, and Apple® QuickTime®. The toolbar may comprise one or more web browser extensions, add-ins, or add-ons. In some embodiments, the toolbar comprises one or more explorer bars, tool bands, or desk bands.

Several plug-in frameworks may be available that may enable development of plug-ins in various programming languages, including, by way of non-limiting examples, C++, Delphi, Java™, PHP, Python™, and VB .NET, or combinations thereof.

Web browsers (also called Internet browsers) are software applications, which may be configured for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) may be configured for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

The systems, media, networks and methods described herein may include software, server, and/or database modules, or use of the same. Software modules may be created using various machines, software, and programming languages. The software modules disclosed herein are implemented in a multitude of ways. A software module may comprise a file, a section of code, a programming object, a programming structure, or combinations thereof. A software module may comprise a plurality of files, a plurality of sections of code, a plurality of programming objects, a plurality of programming structures, or combinations thereof. The one or more software modules may comprise, by way of non-limiting examples, a web application, a mobile application, and a standalone application. In some embodiments, software modules are in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

The platforms, systems, media, and methods disclosed herein may include one or more databases, or use of the same. In view of the disclosure provided herein, many databases are suitable for storage and retrieval of physiological data. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. A database may be web-based. A database may be cloud computing-based. A database may be based on one or more local computer storage devices.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A patch comprising:

a plurality of sensors, supported by the patch, wherein each sensor is configured to collect health related data from a subject to which the patch is attached;

a communication interface configured to wirelessly and directly communicate with a mobile device capable of running a plurality of applications, wherein a first application of the plurality is configured to utilize health data from a first subset of the plurality of sensors on the patch, and wherein a second application of the plurality is configured to utilize health related data from a second subset of the plurality of sensors on the patch different from the first subset of sensors; and one or more processors within the patch configured to selectively activate one or more sensors of the first subset or the second subset to collect the health related data from the selected one or more sensors of the first subset or the second subset in response to a communication with the mobile device based at least in part on a selection of the first or the second application from the plurality of applications running on the mobile device, wherein the communication interface is further configured to transmit the collected health related data.

2. The patch of claim 1, wherein the selection of the first or the second application is based on an amount of data collection, a duration of data collection, or a combination thereof.

3. The patch of claim 1, wherein the plurality of applications: (i) receive information from the plurality of sensors indicating a type of collected health related data, and (ii) display information on the mobile device in a predetermined format based on the type of collected health related data.

4. The patch of claim 1, wherein the plurality of sensors on the patch comprise three or more sensors selected from the group consisting of: ECG, heart rate, heart rate variation, respiration, SpO2, temperature, accelerometer, gyroscope, hydration, and heart sound.

5. The patch of claim 1, wherein the patch comprises one or more of a disposable portion and one or more of a reusable portion.

6. The patch of claim 5, wherein the disposable portion comprises a body layer configured to adhere to the skin of the subject.

7. The patch of claim 6, wherein the body layer comprises an electrical contact configured to convey electrode data to the reusable portion.

8. The patch of claim 5, wherein the reusable portion comprises an electronic module, wherein the communication interface is provided on the electronic module.

9. The patch of claim 5, wherein the reusable portion connects with the disposable portion via one or more magnets.

10. The patch of claim 1, wherein the communication interface further comprises one or more radio transmitters or receivers.

11. The patch of claim 10, wherein the communication interface comprises at least one narrowband radio transmitter, receiver, or transceiver, and at least one ultrawideband radio transmitter, receiver, or transceiver.

12. The patch of claim 1, wherein the plurality of applications comprise two or more use cases selected from the group consisting of: cardiac care, sleep apnea, athlete fitness, infant monitoring, senior living, pet monitoring, gait analysis, mental stress, emotional states, or fall detection.

13. The patch of claim 1, wherein the patch is configured to positioned on the subject's torso to collect the health related data.

14. The patch of claim 1, wherein the plurality of applications output analytics.

15. The patch of claim 1, wherein the plurality of applications are capable of providing analytics for a plurality of use cases by relying on data from the plurality of sensors of the patch without requiring additional data from any other sensors.

16. A method of monitoring health related conditions of a subject, the method comprising:

receiving the transmitted collected health related data from the patch of claim 1, wherein the patch is attached to the subject;

analyzing the transmitted collected health related data; and wirelessly transmitting the analyzed data for display of the information on a wearable device worn by the subject.

17. The method of claim 16, wherein the wearable device is a watch configured to be worn on a wrist of the subject.

18. The method of claim 16, wherein the display of the information on the wearable device is provided as a diagram, time chart, histogram, trend over time, evaluation, statement, message, pie chart, event marker, or a combination thereof.

19. The method of claim 16, further comprising transmitting the information to the cloud.

20. The method of claim 16, wherein the analyzing is performed using one or more machine learning models in the plurality of applications.

* * * * *